United States Patent [19]

Albrecht et al.

[11] 4,242,332
[45] Dec. 30, 1980

[54] 4,5-METHANO-BUFADIENOLIDE-RHAMNOSIDES, THEIR PREPARATION, AND DRUGS CONTAINING THESE COMPOUNDS

[75] Inventors: Hans P. Albrecht; Gerda von Philipsborn, both of Weinheim; Hans U. Siebeneick, Ludwigshafen; Manfred Raschack, Weisenheim, all of Fed. Rep. of Germany

[73] Assignee: BASF Aktiengesellschaft, Fed. Rep. of Germany

[21] Appl. No.: 73,107

[22] Filed: Sep. 6, 1979

[30] Foreign Application Priority Data

Sep. 21, 1978 [DE] Fed. Rep. of Germany ....... 2841074

[51] Int. Cl.³ ..................... A61K 31/705; C07J 19/00
[52] U.S. Cl. ....................................... 424/182; 536/5; 536/6
[58] Field of Search ............................. 536/6; 424/182

[56] References Cited

U.S. PATENT DOCUMENTS 3,726,857   4/1973   Kubinyi ................................... 536/6
3,919,191  11/1975   Haede et al. ............................ 536/6

*Primary Examiner*—Johnnie R. Brown
*Attorney, Agent, or Firm*—Keil & Witherspoon

[57] ABSTRACT

4,5-methano-bufadienolide-rhamnosides of the formula I

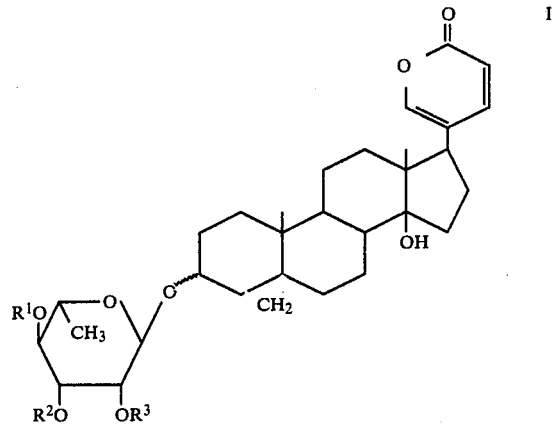

where $R^1$ is hydrogen or alkyl or acyl of 1 to 4 carbon atoms, $R^2$ and $R^3$ are identical or different and each is hydrogen or alkyl or acyl of 1 to 4 carbon atoms, or both together are

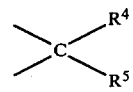

where $R^4$ and $R^5$ are identical or different and each is hydrogen or alkyl or alkoxy of 1 or 2 carbon atoms.

The novel compounds may be used for counteracting cardiac insufficiency.

8 Claims, No Drawings

4,5-METHANO-BUFADIENOLIDE-RHAMNOSIDES, THEIR PREPARATION, AND DRUGS CONTAINING THESE COMPOUNDS

Steroids carrying a methylene bridge on two adjacent carbon atoms have been disclosed. One such compound is cyproterone acetate, which is used as an anti-androgen. Steroids which contain methylene bridges and have effects on the heart have not previously been disclosed.

The present invention provides novel 4,5-methano-bufadienolide-rhamnosides of the forumula I

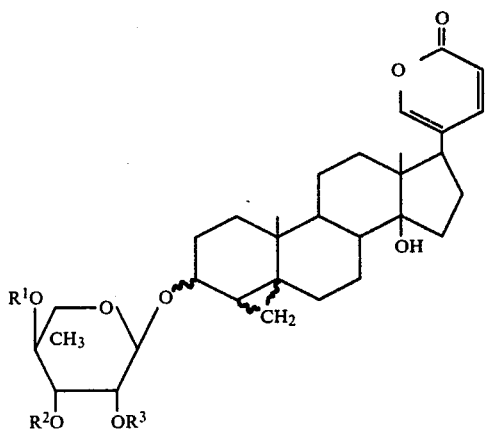

where $R^1$ is hydrogen or alkyl of 1 to 4 carbon atoms or acyl of 1 to 4 carbon atoms, and $R^2$ and $R^3$ are identical or different and each is hydrogen or alkyl of 1 to 4 carbon atoms or acyl of 1 to 4 carbon atoms, or both together are

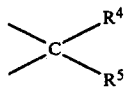

where $R^4$ and $R^5$ are identical or different and each is hydrogen, or alkyl or alkoxy of 1 or 2 carbon atoms.

The invention further provides a process for the preparation of a compound of the formula I, wherein (a) a 3,14-dihydroxy-4,5-methano-14β-bufa-20,22-dienolide of the general formula II

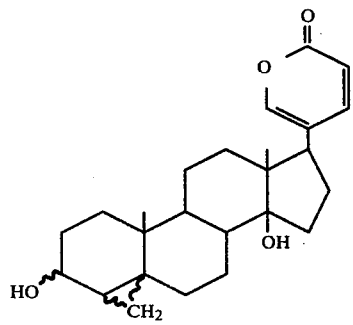

is reacted with a rhamnose derivative of the general formula III

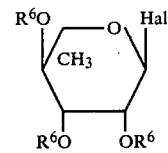

where the $R^6$ groups are acetyl or benzoyl and Hal is halogen, and if desired the resulting compound is hydrolyzed and then if desired etherified and/or if desired a radical

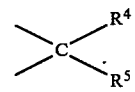

where $R^4$ and $R^5$ have the above meanings, is introduced into the resulting compound, or (b) if the compound of the general formula I to be produced is a cis-methano-proscillaridine derivative, a methylene group is introduced into a compound of the general formula IV

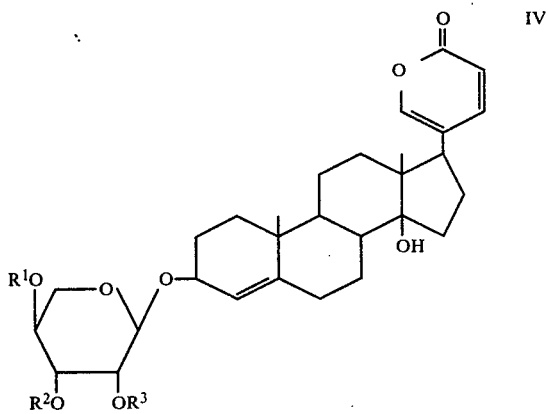

where $R^1$, $R^2$ and $R^3$ have the same meaning as above.

The invention further provides drugs which contain a compound of the formula I.

In the compounds I, $R^1$, $R^2$ and $R^3$ may for example be hydrogen or methyl, ethyl, n-propyl, iso-propyl, n-butyl, iso-butyl, formyl, acetyl, propionyl, n-butyryl or iso-butyryl. $R^4$ and $R^5$ may be methoxy, ethoxy, methyl or ethyl.

The steroidal aglycones II are advantageously reacted with an excess (preferably from 3 to 5 moles) of acylated 1-halorhamnose III. The reaction proceeds well at from 0° to 30° C., so that it can be carried out at room temperature. The reaction is in general carried out in an inert solvent. Examples of inert solvents for the reaction are methylene chloride, ether, tetrahydrofuran, acetonitrile, nitromethane and, preferably, dichloroethane. The reaction time depends on the temperature and is as a rule from 3 to 24 hours. The reaction is advantageously carried out in the presence of an acid acceptor, such as a cyanide, oxide or carbonate of a metal of sub-group 1 or 2 of the periodic table. Examples of such compounds are silver(I) oxide, silver(I) carbonate, mercury(II) oxide, mercury(II) carbonate, cadmium carbonate and, preferably, mercury(II) cyanide.

The compounds thus obtained can be deacylated (hydrolyzed) in a conventional manner; preferably this is achieved with a solution of ammonia in methanol at room temperature, or with potassium bicarbonate in aqueous methanol at from 20° to 70° C.

The etherification of one or more of the free OH groups and the introduction of the radical

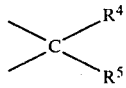

can also take place in a conventional manner.

The addition of a methylene group to a compound IV is advantageously effected by reacting the compound IV with iodomethyl-zinc iodide by the Simmons-Smith method (cf. H. E. Simmons et al., Organic Reactions 20, 1, John Wiley and Sons, 1973). In practice, the preferred method is to add, successively, diiodomethane and a solution of the proscillaridine derivative in an inert solvent, preferably tetrahydrofuran, under a nitrogen atmosphere to a zinc-copper couple obtained by reacting zinc dust and a copper salt, especially CuCl, in ether at the reflux temperature (cf. R. J. Rawson and I. T. Harrison, J. Org. Chem. 35 (1970), 2057). The zinc-copper couple and the diiodomethane are generally used in from about 2-fold to 30-fold, preferably from 3-fold to 10-fold, excess. The reaction proceeds well at 30°–65° C. and is as a rule complete after from 1 to 24 hours.

The addition of the methylene group takes place stereospecifically at the 4,5-double bond of the proscillaridine derivative, in the cis-position to the 3-0 group. It is very surprising that the unsaturated lactone ring is not attacked at the same time.

The novel compounds increase the force of contraction of the heart and may be used in the therapy of cardiac insufficiency.

The novel compounds increase the contractile force of the heart and may be used in the therapy of cardiac insufficiency.

Compared to the cardiac glycosides hitherto accepted in therapy, the novel compounds exhibit a higher activity and a broader therapeutic range.

The activity of the compounds according to the invention, i.e. the increase in force of contraction on an electrically stimulated and spontaneously beating guinea pig auricle, is from 4 to 50 times greater than that of the cardiac glycosides used hitherto in therapy.

The quotient of the arrhythmogenically active dose and the dose required for an increase in force of contraction of a spontaneously beating auricle is from 2 to 10 times greater than with the cardiac glycosides which have found acceptance in therapy. The novel compounds are also distinguished by great stability to acids.

The novel compounds can be administered in a conventional manner, either orally or intravenously.

The dosage depends on the age, condition and weight of the patient and on the administration route. As a rule, the daily dose of active compound is from about 0.003 to 0.06 mg/kg of body weight for either oral or intravenous administration.

The novel compounds can be used in the conventional solid or liquid pharmaceutical forms for administration, e.g. as tablets, capsules, powders, granules, dragees or solutions. These may be prepared in a conventional manner, and to do so the active ingredients can be compounded with the conventional pharmaceutical excipients, such as tablet binders, fillers, preservatives, tablet-disintegrating agents, flow control agents, plasticizers, wetting agents, dispersants, emulsifiers and/or solvents (cf. L. G. Goodman and A. Gilman: The Pharmacological Basis of Therapeutics).

The compounds of the general formula II have not previously been disclosed. They can be prepared by introducing a methylene group into a compound of the general formula

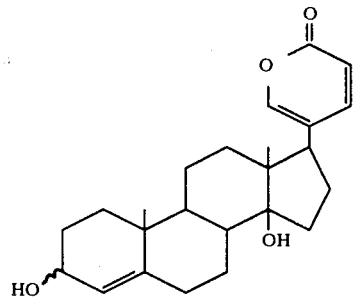

in the manner described above in respect of compounds IV. This only produces the 3α-hydroxy-4α,5-methano and 3β-hydroxy-4β,5-methano compounds. However, oxidation of these compounds with chromic acid/sulfuric acid in acetone by the Jones method (J. Chem. Soc. 1953, 2555), followed by reduction with sodium borohydride in methanol at room temperature gives the 3α-hydroxy-4β,5-methano 3β-hydroxy-4α,5-methano compounds.

The examples which follow illustrate the invention. The Rf values were determined on silica gel pre-coated plates from Merck, Darmstadt, using a 5:1 methylene chloride/acetone mixture (mobile phase A) and a 10:1 methylene chloride/methanol mixture (mobile phase B).

EXAMPLE 1

(a) 4.0 g (7.5 millimoles) of 2,3,4-tri-O-benzoyl-α-L-rhamnopyranosyl bromide, 4.0 g of mercury(II) cyanide and 5 g of molecular sieve A 4 are added to 0.8 g (2.0 millimoles) of 3β,14-dihydroxy-4β,5-methano-5β,14β-bufa-20,22-dienolide (melting point 172°–180° C.) in 40 ml of anhydrous 1,2-dichloroethane. The reaction mixture is stirred at room temperature and the course of the reaction is followed by thin layer chromatography (using mobile phase A).

After 1.5 hours, chloroform (600 ml) is added, the mixture is filtered over kieselguhr and the filtrate is washed with 20% strength aqueous potassium iodide solution (2×150 ml) and water (2×100 ml), dried over sodium sulfate and evaporated.

Chromatography of the residue on a silica gel column (with elution with a 10:1 methylene chloride/acetone mixture) gives 14-hydroxy-4β,5-methano-3β[(2,3,4-tri-O-benzoyl-α-L-rhamnopyranosyl)oxy]-5β,14β-bufa-20,22-dienolide.

Melting point: 153°–158° C. (from methylene chloride/ether/hexane);

$[\alpha]_D^{20} = +18°$ (c=0.5 in chloroform);

UV spectrum (methanol): $\lambda_{max}$ (1 g $\epsilon$)=228 (4.21), 283 (3.82) and 298 (3.65);

Rf=0.56 (mobile phase A).

(b) 5 ml of a 5% strength aqueous potassium bicarbonate solution are added to 857 mg (1 millimole) of the compound obtained according to a), in 50 ml of methanol. After 70 hours at room temperature, 300 ml of chloroform are added to the mixture, which is then washed with a small amount of water and evaporated.

Chromatography of the residue on a silica gel column (elution with a 10:1 methylene chloride/methanol mixture) and crystallization of the residue from an ethanol/water mixture gives 305 mg (56%) of 14-hydroxy-4β,5-methano-3β-[(α-L-rhamnopyranosyl)oxy]-5β,14β-bufa-20,22-dienolide.

Melting point: 251°-258° C;

$[\alpha]_D^{20} = -105°$ (c=0.5 in a 10:1 chloroform/methanol mixture);

UV spectrum (methanol): $\lambda_{max}$ (1 g ϵ)=297 (3.75);

Rf=0.17 (mobile phase B).

$C_{21}H_{44}O_8$ (544.7) Calculated: C 68.36, H 8.14.

Found: C 67.8, H 8.2.

EXAMPLE 2

A suspension of 6.5 g (100 g atoms) of zinc dust and 1.0 g (10 millimoles) of copper(I) chloride in 30 ml of ether are refluxed in a nitrogen atmosphere, with vigorous stirring, at a bath temperature of 40°-45° C. After 30 minutes, 8.1 ml (100 millimoles) of diiodomethane are added dropwise in the course of 5-10 minutes, after which a solution of 5.7 g (10 millimoles) of 14-hydroxy-3β-[(2,3-0-isopropylidene-α-L-rhamnopyranosyl)-oxy]-14β-bufa-4,20,22-trienolide (=proscillaridine-2',3'-acetonide) in 50 ml of tetrahydrofuran is added slowly.

The reaction is followed by means of thin layer chromatography (mobile phase A). After 3 to 4 hours at a bath temperature of 45°-55° C., the reaction is complete. The reaction mixture is brought to a volume of 100 ml with tetrahydrofuran, 10 ml of a saturated aqueous ammonium chloride solution are added slowly whilst cooling with ice, and the mixture is then filtered over kieselguhr. The filtrate is taken up in methylene chloride (1,000 ml), washed with 10% strength aqueous sodium thiosulfate solution (2×100 ml), saturated aqueous sodium bicarbonate solution (100 ml) and water (2×100 ml), dried over sodium sulfate and evaporated under reduced pressure. Chromatography of the residue on a silica gel column using an 8:1 methylene dichloride/acetone mixture, and crystallization of the pure fraction from ethanol, gives 2.85 g (49%) of 14-hydroxy-4β,5-methano-3β-[(2,3-0-isopropylidene-α-L-rhamnopyranosyl)-oxy]-5β,14β-bufa-20,22-dienolide.

Melting point: 229°-232° C;

$[\alpha]_D^{20} = -94°$ (c=0.5 in chloroform);

UV spectrum (methanol): $\lambda_{max}$ (1 g ϵ)=298 nm (3.75);

Rf=0.54 (mobile phase B).

$C_{34}H_{48}O_8$ (584.7) Calculated: C 69.84, H 8.27. Found: C 69.57, H 8.11.

The following are obtained by similar methods:

14-Hydroxy-4β,5-methano-3β-[(2,3-0-isopropylidene-4-0-methyl-α-L-rhamnopyranosyl)oxy]-5β,14β-bufa-20,22-dienolide, yield 46%.

Melting point: 160°-163° C. (methylene chloride/ether/hexane);

$[\alpha]_D^{20} = -96°$ (c=0.5 inch chlorform);

UV spectrum (methanol): $\lambda_{max}$ (1 g ϵ)=298 nm (3.75);

Rf=0.47 (mobile phase A).

$C_{35}H_{50}O_8$ (598.8) Calculated: C 70.20, H 8.42. Found: C 70.3, H 8.5.

14-Hydroxy-4β,5-methano-3β-[(2,3-0-ethoxymethylidene-α-L-rhamnopyranosyl)oxy]-5β,14β-bufa-20,22-dienolide, yield 41%.

Melting point: 245°-250° C. (methylene chloride/methanol/ether;

$[\alpha]_D^{20} = -80°$ (c=0.5 in chloroform);

UV spectrum (methanol): $\lambda_{max}$ (1 g ϵ)=2.98 nm (3.76);

Rf=0.43 (mobile phase B).

$C_{34}H_{48}O_9$ (600.7) Calculated: C 67.97, H 8.05. Found: C 67.75, H 8.00.

EXAMPLE 3

20 ml of 1 N HCl are added to 2.9 g (5.0 millimoles) of 14-hydroxy-4β,5-methano-3β-[(2,3-0-isopropylidene-α-L-rhamnopyranosyl)oxy]-s5β,14β-bufa-20,22-dienolide (Example 2) in 100 ml of tetrahydrofuran whilst stirring at room temperature. The course of the reaction is followed by means of thin layer chromatography (mobile phase B). After 32 hours, the reaction mixture is neutralized by adding 2 g of sodium bicarbonate, taken up in 800 ml of a 10:1 chloroform/methanol mixture, washed with a small amount of water and evaporated under reduced pressure. Chromatography of the residue on a silica gel column (elution with a 10:1 methylene dichloride/methanol mixture) and subsequent crystallization of the pure fraction from ethanol gives 1.4 g (51%) of 14-hydroxy-4β,5-methano-3β-[(α-L-rhamnopyranosyl)oxy]-5β,14β-bufa-20-dienolide.

Melting point: 249°-253° C.;

$[\alpha]_D^{20} = -114°$ (c=0.5 in a 10:1 methanol/chloroform mixture);

UV spectrum (methanol): $\lambda_{max}$ (1 g ϵ)=297 (3.75);

Rf=0.17 (mobile phase B).

The following compound is obtained by a similar method:

14-Hydroxy-4β,5-methano-3β-[(4-0-methyl-α-L-rhamnopyranosyl)oxy]-5β,14β-bufa-20,22-dienolide, yield 41%.

Melting point: 220°-234° C.;

$[\alpha]_D^{20} = -109°$ (c=0.5 in chloroform);

UV spectrum (methanol): $\lambda_{max}$ (1 g ϵ)=298 nm (3.76);

Rf=0.28 (mobile phase B)

$C_{32}H_{46}O_6$ (558.7) calculated: C 68.79, H 8.30. Found: C 68.8, H 8.3.

EXAMPLE 4

Tablets of the following composition are pressed in the conventional manner on a tableting press:

0.20 mg of 14-hydroxy-4β,5-methane-3β-[(α-L-rhamnopyranosyl)oxy]-5β,14β-bufa-20,22-dienolide 15.0 mg of corn starch 1.35 mg of gelatin 4.5 mg of lactose 2.25 mg of talc 0.22 mg of Aerosil ® (chemically pure silica in a sub-microscopic state of division) and 0.67 mg of potato starch (as a 6% paste).

EXAMPLE 5

Dragees of the following composition are prepared in the convention manner:

0.30 mg of 14-hydroxy-4β,5-methano-3β-[(2,3-0-isopropylidene-α-L-rhamnopyranosyl)-oxy]-5β, 14β-bufa-20,22-dienolide 17.0 mg of core composition
16.0 mg of sugar-coating composition The core composition consists of 9 parts of corn starch, 3 parts of lactose and 1 part of Luviskol ® VA 64 (60:40 vinylpyrrolidone/vinyl acetate copolymer, cf. Pharm. Ind. 1962, 586). The sugar-coating composition consists of 5 parts of sucrose, 2 parts of corn starch, 2 parts of calcium carbonate and 1 part of talc. The dragees thus prepared are subsequently provided with a coating which is resistant to gastric juices.

EXAMPLE 6

1 g of 14-hydroxy-4β,5-methano-3β-[(4-O-methyl-α-L-rhamnopyranosyl)-oxy]-5β,14β-bufa-20,22-dienolide is dissolved in 10 liters of water. The solution is brought to pH 3.5 with 0.1 N sodium acetate and made isotonic by adding sodium chloride. It is then sterile-packed in ampoules of 2 ml capacity.

We claim:

1. A 4,5-Methano-bufadienolide-rhamnoside of the formula I

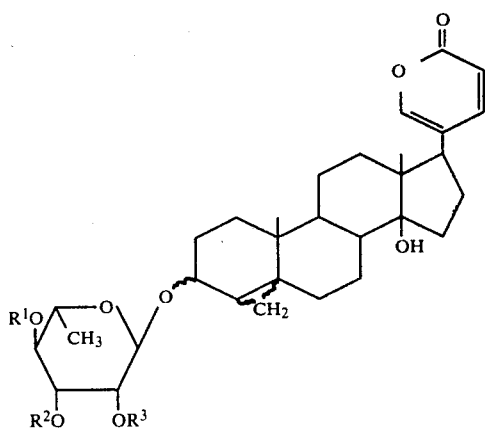

where $R^1$ is hydrogen or alkyl of 1 to 4 carbon atoms or acyl of 1 to 4 carbon atoms, and $R^2$ and $R^3$ are identical or different and each is hydrogen or alkyl of 1 to 4 carbon atoms or acyl of 1 to 4 carbon atoms, or both together are

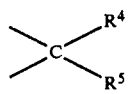

where $R^4$ and $R^5$ are identical or different and each is hydrogen, alkyl or alkoxy of 1 or 2 carbon atoms.

2. A therapeutic composition consisting essentially of a pharmaceutical excipient and an effective amount of a compound according to claim 1 as the active ingredient.

3. 14-Hydroxy-4β,5-methano-3β-[(α-L-rhamnopyraosyl)-oxy]-5β,14β-bufa-20,22-dienolide.

4. 14-Hydroxy-4β,5-methano-3β-[(2,3-O-isopropylidene-α-rhamnopyranosyl) oxy]-5β,14β-bufa-20,22-dienolide.

5. 14-Hydroxy-4β,5-methano-3β-[(2,3-O-isopropylidene-4-O-methyl-α-L-rhamnopyranosyl)oxy]-5β,14β-bufa-20,22-dienolide.

6. 14-Hydroxy-4β,5-methano-3β-[(2,3-O-ethoxymethylidene-α-L-rhamnopyranosyl)oxy]-5β,14β-bufa-20,22-dienolide.

7. 14-Hydroxy-4β,5-methano-3β-[(4-O-methyl-α-L-rhamnopyranosyl)oxy]-5β,14β-bufa-20,22-dienolide.

8. The method of treating cardiac insufficiency in a patient suffering therefrom which consists essentially of administering either orally or intravenously to the patient a pharmaceutically acceptable composition containing an effective amount of a compound of claim 1.

* * * * *

UNITED STATES PATENT AND TRADEMARK OFFICE
CERTIFICATE OF CORRECTION

PATENT NO. : 4,242,332
DATED : December 30, 1980
INVENTOR(S) : H.P. Albrecht, G. von Philipsborn, H.U. Siebeneick, and M. Raschack It is certified that error appears in the above—identified patent and that said Letters Patent is hereby corrected as shown below:

IN THE ABSTRACT

In the formula I, the part of the formula which reads:

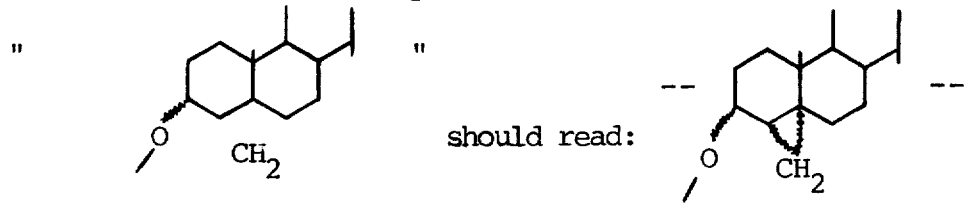

IN THE CLAIMS

Claim 1, last line, after "hydrogen", the comma (,) should be deleted and --or-- should be inserted in its place.

Claim 3, lines 20-21, "rhamnopyraosyl" should read --rhamnopyranosyl--.

Signed and Sealed this

Twenty-third Day of June 1981

[SEAL]

Attest:

RENE D. TEGTMEYER

Attesting Officer *Acting Commissioner of Patents and Trademarks*